United States Patent
Smith et al.

(10) Patent No.: US 11,426,228 B2
(45) Date of Patent: Aug. 30, 2022

(54) RF OUTPUT STAGE SWITCHING MECHANISM

(71) Applicant: Medtronic Advanced Energy LLC, Minneapolis, MN (US)

(72) Inventors: Jesse A. Smith, Portsmouth, NH (US); David Hubelbank, Manchester, NH (US); Duane Marion, Superior, CO (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 552 days.

(21) Appl. No.: 16/530,479

(22) Filed: Aug. 2, 2019

(65) Prior Publication Data

US 2019/0350638 A1    Nov. 21, 2019

Related U.S. Application Data

(62) Division of application No. 14/927,999, filed on Oct. 30, 2015, now Pat. No. 10,405,915.
(Continued)

(51) Int. Cl.
*A61B 18/12* (2006.01)
*A61B 18/00* (2006.01)
*A61B 18/14* (2006.01)

(52) U.S. Cl.
CPC ...... *A61B 18/1233* (2013.01); *A61B 18/1206* (2013.01); *A61B 18/1402* (2013.01); *A61B 18/148* (2013.01); *A61B 2018/0016* (2013.01); *A61B 2018/00178* (2013.01); *A61B 2018/00607* (2013.01); *A61B 2018/00642* (2013.01); *A61B 2018/00648* (2013.01);
(Continued)

(58) Field of Classification Search
None
See application file for complete search history.

(56) References Cited

U.S. PATENT DOCUMENTS

| | | |
|---|---|---|
| 39,358 A | 7/1863 | Smith |
| 41,921 A | 3/1864 | Holmes |

(Continued)

FOREIGN PATENT DOCUMENTS

| | | |
|---|---|---|
| CN | 102641152 | 3/2014 |
| DE | 3420339 | 1/1985 |
| EP | 2474165 | 7/2012 |

OTHER PUBLICATIONS

PCT International Search Report dated Jan. 27, 2017, 4 pages.
(Continued)

*Primary Examiner* — Ronald Hupczey, Jr.
(74) *Attorney, Agent, or Firm* — Christopher & Weisberg, P.A.

(57) ABSTRACT

An electrosurgical unit including a radiofrequency generator configured to generate electrosurgical energy. The radiofrequency generator includes a first receptacle configured to electrically couple with an electrosurgical hand piece configured to deliver bipolar radiofrequency energy. A second receptacle is included and configured to electrically couple with an electrosurgical hand piece configured to deliver monopolar radiofrequency energy. The radiofrequency generator includes a relay circuit configured to allow simultaneous radiofrequency energy delivery to the electrosurgical hand pieces in the first receptacle and the second receptacle.

5 Claims, 2 Drawing Sheets

Related U.S. Application Data

(60) Provisional application No. 62/164,930, filed on May 21, 2015, provisional application No. 62/073,705, filed on Oct. 31, 2014.

(52) U.S. Cl.
CPC ........... *A61B 2018/00666* (2013.01); *A61B 2018/00702* (2013.01); *A61B 2018/00767* (2013.01); *A61B 2018/00827* (2013.01); *A61B 2018/00875* (2013.01); *A61B 2018/00892* (2013.01); *A61B 2018/124* (2013.01); *A61B 2018/126* (2013.01); *A61B 2018/1253* (2013.01); *A61B 2018/1286* (2013.01)

(56) References Cited

U.S. PATENT DOCUMENTS

| | | | |
|---|---|---|---|
| 411,004 | A | 9/1889 | Billings |
| 4,244,371 | A | 1/1981 | Farin |
| 4,473,075 | A | 9/1984 | Rexroth |
| 404,004 | A | 5/1989 | Hovey |
| 4,903,696 | A | 2/1990 | Stasx et al. |
| 5,282,799 | A | 2/1994 | Rydell |
| 5,300,068 | A | 4/1994 | Rosar et al. |
| 5,352,868 | A | 10/1994 | Denen et al. |
| 5,438,302 | A | 8/1995 | Goble |
| 5,472,442 | A | 12/1995 | Klicek |
| 5,573,424 | A | 11/1996 | Poppe |
| 5,582,610 | A | 12/1996 | Grossi et al. |
| 5,599,349 | A | 2/1997 | D'Amelio |
| 5,647,869 | A | 7/1997 | Goble et al. |
| 5,669,906 | A | 9/1997 | Grossi et al. |
| 5,766,153 | A | 6/1998 | Eggers et al. |
| 5,860,975 | A | 1/1999 | Goble et al. |
| 5,888,198 | A | 3/1999 | Eggers et al. |
| 5,944,715 | A | 8/1999 | Goble et al. |
| 6,004,319 | A | 12/1999 | Goble et al. |
| 6,013,076 | A | 1/2000 | Goble et al. |
| 6,015,406 | A | 1/2000 | Goble et al. |
| 6,027,501 | A | 2/2000 | Goble et al. |
| 6,039,734 | A | 3/2000 | Goble |
| 6,056,746 | A | 5/2000 | Goble et al. |
| 6,074,386 | A | 6/2000 | Goble et al. |
| 6,090,106 | A | 7/2000 | Goble et al. |
| 6,093,186 | A | 7/2000 | Goble |
| 6,100,920 | A | 8/2000 | Miller et al. |
| 6,151,381 | A | 11/2000 | Grodzins et al. |
| 6,174,308 | B1 | 1/2001 | Goble et al. |
| 6,197,025 | B1 | 3/2001 | Grossi et al. |
| 6,210,405 | B1 | 4/2001 | Goble et al. |
| 6,228,081 | B1 | 5/2001 | Goble |
| 6,234,178 | B1 | 5/2001 | Goble et al. |
| 6,238,388 | B1 | 5/2001 | Ellman et al. |
| 6,261,286 | B1 | 7/2001 | Goble et al. |
| 6,277,114 | B1 | 8/2001 | Bullivant et al. |
| 6,293,942 | B1 | 9/2001 | Goble et al. |
| 6,298,255 | B1 | 10/2001 | Cordero et al. |
| 6,306,134 | B1 | 10/2001 | Goble et al. |
| 6,322,494 | B1 | 11/2001 | Bullivant et al. |
| 6,325,799 | B1 | 12/2001 | Goble |
| 6,336,926 | B1 | 1/2002 | Goble |
| 6,364,877 | B1 | 4/2002 | Goble et al. |
| 6,385,059 | B1 | 5/2002 | Telefus et al. |
| 6,398,781 | B1 | 6/2002 | Goble et al. |
| 6,416,509 | B1 | 7/2002 | Gobel et al. |
| 6,482,202 | B1 | 11/2002 | Gobel et al. |
| 6,488,678 | B2 | 12/2002 | Sherman |
| 6,491,690 | B1 | 12/2002 | Gobel et al. |
| 6,508,815 | B1 | 1/2003 | Strul et al. |
| 6,544,260 | B1 | 4/2003 | Markel et al. |
| 6,547,786 | B1 | 4/2003 | Goble |
| 6,557,559 | B1 | 5/2003 | Eggers et al. |
| 6,558,379 | B1 | 5/2003 | Batchelor et al. |
| 6,565,560 | B1 | 5/2003 | Gobel et al. |
| 6,565,561 | B1 | 5/2003 | Gobel et al. |
| 6,582,427 | B1 | 6/2003 | Gobel et al. |
| 6,611,141 | B1 | 8/2003 | Schulz et al. |
| 6,723,091 | B2 | 4/2004 | Gobel et al. |
| 6,758,846 | B2 | 7/2004 | Gobel et al. |
| 6,761,716 | B2 | 7/2004 | Kadhiresan et al. |
| 6,808,525 | B2 | 10/2004 | Latterell et al. |
| 6,832,998 | B2 | 12/2004 | Goble |
| 6,843,789 | B2 | 1/2005 | Goble |
| 6,893,435 | B2 | 5/2005 | Goble |
| 6,923,803 | B2 | 8/2005 | Goble |
| 6,929,641 | B2 | 8/2005 | Gobel et al. |
| 6,942,660 | B2 | 9/2005 | Pantera et al. |
| 6,966,907 | B2 | 11/2005 | Goble |
| 6,984,231 | B2 | 1/2006 | Gobel et al. |
| 7,001,380 | B2 | 2/2006 | Goble |
| 7,094,231 | B1 | 8/2006 | Ellman et al. |
| 7,137,980 | B2 | 11/2006 | Buysse et al. |
| 7,147,637 | B2 | 12/2006 | Goble |
| 7,153,300 | B2 | 12/2006 | Goble |
| 7,195,627 | B2 | 3/2007 | Amoah et al. |
| 7,201,750 | B1 | 4/2007 | Eggers et al. |
| 7,211,081 | B2 | 5/2007 | Goble |
| 7,211,084 | B2 | 5/2007 | Gobel et al. |
| 7,214,224 | B2 | 5/2007 | Goble |
| 7,255,696 | B2 | 8/2007 | Gobel et al. |
| 7,278,994 | B2 | 10/2007 | Goble |
| 7,282,048 | B2 | 10/2007 | Gobel et al. |
| 7,300,436 | B2 | 11/2007 | Penny et al. |
| 7,322,975 | B2 | 1/2008 | Gobel et al. |
| 7,335,199 | B2 | 2/2008 | Gobel et al. |
| 7,344,532 | B2 | 3/2008 | Gobel et al. |
| 7,429,261 | B2 | 9/2008 | Kunis et al. |
| 7,442,191 | B2 | 10/2008 | Hovda et al. |
| 7,491,199 | B2 | 2/2009 | Goble |
| 7,651,513 | B2 | 1/2010 | Teoh et al. |
| 7,674,263 | B2 | 3/2010 | Ryan |
| 7,699,846 | B2 | 4/2010 | Ryan |
| 7,708,733 | B2 | 5/2010 | Sanders et al. |
| 7,717,910 | B2 | 5/2010 | Goble |
| 7,799,020 | B2 | 9/2010 | Shores et al. |
| 7,850,684 | B2 | 12/2010 | Marshall et al. |
| 7,854,736 | B2 | 12/2010 | Ryan |
| 7,855,727 | B2 | 12/2010 | Adler et al. |
| 7,887,534 | B2 | 2/2011 | Hamel et al. |
| 7,887,536 | B2 | 2/2011 | Johnson et al. |
| 7,896,877 | B2 | 3/2011 | Hall et al. |
| 7,993,332 | B2 | 8/2011 | Gobel et al. |
| 8,002,769 | B2 | 8/2011 | Gobel et al. |
| 8,082,043 | B2 | 12/2011 | Sharkey et al. |
| 8,175,590 | B2 | 5/2012 | Hamel et al. |
| 8,192,424 | B2 | 6/2012 | Woloszko |
| 8,226,680 | B2 | 7/2012 | Wallace |
| 8,241,284 | B2 | 8/2012 | Dycus et al. |
| 8,246,616 | B2 | 8/2012 | Amoah et al. |
| 8,251,989 | B1 | 8/2012 | Newton et al. |
| 8,257,350 | B2 | 9/2012 | Marion |
| 8,273,084 | B2 | 9/2012 | Kunis et al. |
| 8,273,085 | B2 | 9/2012 | Park et al. |
| 8,333,760 | B2 | 12/2012 | Roggan et al. |
| 8,355,799 | B2 | 1/2013 | Marion et al. |
| 8,444,638 | B2 | 5/2013 | Woloszko et al. |
| 8,452,422 | B2 | 5/2013 | Desinger et al. |
| 8,512,340 | B2 | 8/2013 | Easley et al. |
| 8,551,088 | B2 | 10/2013 | Falkenstein et al. |
| 8,562,598 | B2 | 10/2013 | Falkenstein et al. |
| 8,568,405 | B2 | 10/2013 | Cox et al. |
| 8,574,187 | B2 | 11/2013 | Marion |
| 8,579,894 | B2 | 11/2013 | Falkenstein et al. |
| 8,597,287 | B2 | 12/2013 | Benamou et al. |
| 8,617,151 | B2 | 12/2013 | Denis et al. |
| 8,657,817 | B2 | 2/2014 | Fischer et al. |
| 8,672,934 | B2 | 3/2014 | Benamou et al. |
| 8,685,018 | B2 | 4/2014 | Cox et al. |
| 8,696,659 | B2 | 4/2014 | Marion |
| 8,747,399 | B2 | 6/2014 | Woloszko et al. |
| 8,747,401 | B2 | 6/2014 | Gonzalez et al. |
| 8,784,415 | B2 | 7/2014 | Malackowski et al. |
| 8,790,335 | B2 | 7/2014 | Gilbert |

(56) References Cited

U.S. PATENT DOCUMENTS

| | | |
|---|---|---|
| 8,801,705 B2 | 8/2014 | Sanders et al. |
| 8,870,866 B2 | 10/2014 | Woloszko |
| 8,900,226 B2 | 12/2014 | Silig et al. |
| 8,915,910 B2 | 12/2014 | Falkenstein et al. |
| 8,920,412 B2 | 12/2014 | Fritz et al. |
| 8,932,291 B2 | 1/2015 | Orszulak |
| 9,008,757 B2 | 4/2015 | Wu |
| 9,066,735 B2 | 6/2015 | Williams |
| 9,095,358 B2 | 8/2015 | Woloszko et al. |
| 9,099,863 B2 | 8/2015 | Smith et al. |
| 9,138,282 B2 | 9/2015 | Marion |
| 2001/0014003 A1 | 8/2001 | Dible |
| 2003/0050633 A1 | 3/2003 | Ellman et al. |
| 2003/0083652 A1 | 5/2003 | Markel |
| 2003/0181964 A1 | 9/2003 | Sharkey et al. |
| 2004/0199175 A1 | 10/2004 | Jaeger et al. |
| 2005/0113820 A1 | 5/2005 | Goble et al. |
| 2005/0177184 A1 | 8/2005 | Easley |
| 2006/0004396 A1 | 1/2006 | Easley et al. |
| 2006/0106375 A1 | 5/2006 | Werneth et al. |
| 2006/0142753 A1 | 6/2006 | Francischelli et al. |
| 2006/0149225 A1 | 7/2006 | McClurken |
| 2007/0073334 A1 | 3/2007 | Ramzipoor |
| 2007/0083193 A1 | 4/2007 | Werneth et al. |
| 2007/0083195 A1 | 4/2007 | Werneth et al. |
| 2007/0085496 A1 | 4/2007 | Philipp et al. |
| 2007/0104610 A1 | 5/2007 | Houston et al. |
| 2007/0167941 A1 | 7/2007 | Hamel et al. |
| 2007/0225550 A1 | 9/2007 | Gattani et al. |
| 2008/0082095 A1 | 4/2008 | Shores et al. |
| 2008/0108940 A1 | 5/2008 | Sharkey et al. |
| 2008/0281312 A1 | 11/2008 | Werneth et al. |
| 2008/0281322 A1 | 11/2008 | Sherman et al. |
| 2008/0287948 A1* | 11/2008 | Newton ............. A61B 18/1206 606/50 |
| 2009/0182325 A1 | 7/2009 | Werneth et al. |
| 2009/0275940 A1 | 11/2009 | Malackowski et al. |
| 2010/0241115 A1 | 9/2010 | Benamou et al. |
| 2010/0241116 A1 | 9/2010 | Benamou et al. |
| 2010/0324550 A1 | 12/2010 | Morgan et al. |
| 2010/0331666 A1 | 12/2010 | Wallace |
| 2011/0178515 A1 | 7/2011 | Bloom et al. |
| 2011/0270237 A1 | 11/2011 | Werneth et al. |
| 2012/0095457 A1 | 4/2012 | Morgan et al. |
| 2012/0136346 A1 | 5/2012 | Condie et al. |
| 2012/0136347 A1 | 5/2012 | Brustad et al. |
| 2012/0136348 A1 | 5/2012 | Condie et al. |
| 2012/0157985 A1 | 6/2012 | Ballou et al. |
| 2012/0197243 A1 | 8/2012 | Sherman et al. |
| 2012/0215216 A1 | 8/2012 | Friedrichs et al. |
| 2012/0265196 A1 | 10/2012 | Turner et al. |
| 2013/0053840 A1 | 2/2013 | Krapohl et al. |
| 2013/0253502 A1 | 9/2013 | Aronow et al. |
| 2013/0274729 A1 | 10/2013 | Orszulak |
| 2014/0018795 A1 | 1/2014 | Shilev et al. |
| 2014/0025061 A1 | 1/2014 | Benamou |
| 2014/0039517 A1 | 2/2014 | Bowling et al. |
| 2014/0052123 A1 | 2/2014 | Benamou et al. |
| 2014/0200621 A1 | 7/2014 | Malackowski et al. |
| 2014/0232316 A1 | 8/2014 | Philipp |
| 2014/0276750 A1 | 9/2014 | Gilbert |
| 2014/0276754 A1 | 9/2014 | Gilbert et al. |
| 2014/0276768 A1 | 9/2014 | Juergens et al. |
| 2014/0324039 A1 | 10/2014 | Malackowski et al. |
| 2015/0088118 A1 | 3/2015 | Gilbert et al. |
| 2015/0230861 A1 | 8/2015 | Woloszko et al. |

OTHER PUBLICATIONS

Valleylab$_{TM}$, Service Manual, Force FX™-SC Electrosurgical Generator with Instant Response™ Technology, Sep. 2000, pp. 1-218.

Force 4 Service Manual, May 1, 1985, Valleylab Part No. A945 100 055A, pp. 1-144.

* cited by examiner

RF OUTPUT STAGE SWITCHING MECHANISM

CROSS-REFERENCE TO RELATED APPLICATION

This application is a divisional of U.S. patent application Ser. No. 14/927,999, filed Oct. 30, 2015 and is related to and claims priority to U.S. Provisional Patent Application Ser. No. 62/073,705, filed Oct. 31, 2014, entitled COMBINATION PEAK PLASMA AND TRANSCOLLATION TIP, and claims priority to U.S. Provisional Patent Application Ser. No. 62/164,930, filed May 21, 2015, entitled ELECTROSURGICAL GENERATOR the entirety of which is incorporated herein by reference.

STATEMENT REGARDING FEDERALLY SPONSORED RESEARCH OR DEVELOPMENT n/a

TECHNICAL FIELD

The present invention relates to an electrosurgical unit having a radiofrequency generator, and in particular, relay circuitry configured to allow simultaneous operation of two electrosurgical hand pieces.

BACKGROUND

Electrosurgery is the application of radiofrequency electrical energy to biological tissue to cut, coagulate, desiccate, or fulgurate tissue. Electrosurgical units typically include an electrosurgical generator configured to supply the electrical energy, and an electrosurgical hand piece configure to electrically couple with the electrosurgical unit and deliver the electrical energy to the tissue. There are two modes by which electrosurgical energy is typically applied to tissue. Monopolar electrosurgery is the passage of high-frequency current to tissue through a single active electrode to a return electrode positioned remotely from the electrode where heating does not take place. Bipolar electrosurgery is the passage of high-frequency current to tissue between two commonly-supported active electrodes where both actively heat tissue.

Monopolar configurations are widely used for general cutting and coagulation procedures, as the current field has a high current density near the active electrode. Bipolar configurations are widely used for procedures such as coagulation and ablation of tissue where a volume of tissue is positioned between two active electrodes. The current field in a bipolar device is contained between the two electrodes. Thus, it may be advantageous to use both a bipolar hand piece and a monopolar hand piece during the same procedure and at the same time to provide for multiple treatment modalities and reduce surgical times. However, current electrosurgical units only allow for the surgeon to use either one electrosurgical hand piece at time or to use two electrosurgical hand pieces at a time, but those two electrosurgical hand pieces must operate in monopolar mode only. Thus, no electrosurgical units exist that allow for the simultaneous operation of a monopolar hand piece and a bipolar hand piece.

SUMMARY

The present invention advantageously provides for an electrosurgical unit including a radiofrequency generator configured to generate electrosurgical energy. The radiofrequency generator includes a first receptacle configured to electrically couple with an electrosurgical hand piece configured to deliver bipolar radiofrequency energy. A second receptacle is included and configured to electrically couple with an electrosurgical hand piece configured to deliver monopolar radiofrequency energy. The radiofrequency generator includes a relay circuit configured to allow simultaneous radiofrequency energy delivery to the electrosurgical hand pieces in the first receptacle and the second receptacle.

In another embodiment, the electrosurgical unit includes a radiofrequency generator configured to generate electrosurgical energy. The radiofrequency generator includes a first receptacle configured to electrically couple with a first electrosurgical hand piece configured to deliver bipolar radiofrequency energy. A second receptacle configured to electrically couple with: a second electrosurgical hand piece configured to deliver both monopolar radiofrequency energy and bipolar radiofrequency energy and a third electrosurgical hand piece configured to deliver monopolar radiofrequency energy is included. The radiofrequency generator includes a relay circuit configured to allow simultaneous radiofrequency energy delivery to the electrosurgical hand pieces in the first receptacle and the second receptacle when the first electrosurgical hand piece is electrically coupled to the first receptacle, and at least one of: the second electrosurgical hand piece is electrically coupled to the second receptacle and the second hand piece is activated to deliver monopolar radiofrequency energy, and the third electrosurgical hand piece is electrically coupled to the second receptacle.

In yet another embodiment, the electrosurgical unit includes a radiofrequency generator configured to generate electrosurgical energy. The radiofrequency generator includes a first receptacle configured to electrically couple with a first electrosurgical hand piece configured to deliver bipolar radiofrequency energy, the first receptacle being electrically coupled to an active bipolar radiofrequency output and a return bipolar radiofrequency output. A second receptacle is configured to electrically couple with at least one of: a second electrosurgical hand piece configured to deliver both monopolar radiofrequency energy and bipolar radiofrequency energy; and a third electrosurgical hand piece configured to deliver monopolar radiofrequency energy. The second receptacle is electrically coupled to the return bipolar radiofrequency output. The radiofrequency generator includes a relay circuit configured to allow simultaneous radiofrequency energy delivery to the electrosurgical hand pieces in the first receptacle and the second receptacle when the first electrosurgical hand piece is electrically coupled to the first receptacle and at least one of: the second electrosurgical hand piece is electrically coupled to the second receptacle and the second hand piece is activated to deliver monopolar radiofrequency energy and the third electrosurgical hand piece is electrically coupled to the second receptacle.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

As used here, relational terms, such as "first" and "second," "top" and "bottom," "front and rear," and the like, may be used solely to distinguish one entity or element from another entity or element without necessarily requiring or implying any physical or logical relationship or order between such entities or elements.

Figure 1:
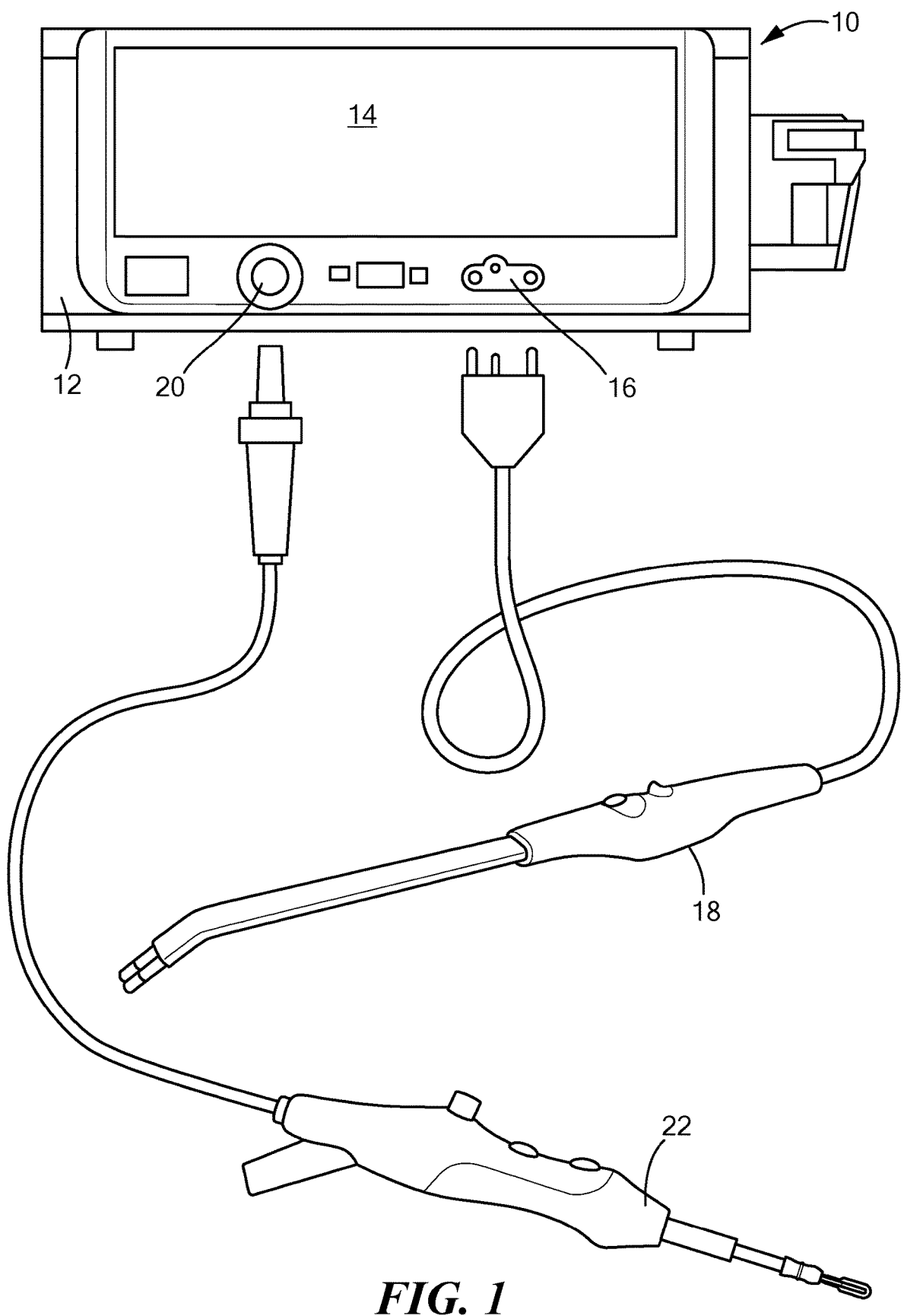
FIG. 1 is a front perspective view of an electrosurgical hand piece and electrosurgical unit constructed in accordance with the principles of the present application.

Referring now to the drawings in which like reference designators refer to like elements, there is shown in FIG. 1 and exemplary electrosurgical unit ("ESU") constructed in accordance with the principles of the present application and designated generally as "10." The ESU 10 may include a radiofrequency generator 12 configured to house and electrically couple the components and circuits of the ESU 10 and a touch actuated display 14 configured to receive energy requests from one or more electrosurgical hand pieces that electrically couple to the radiofrequency generator 12, display treatment progress and measurements, for example, impedance, and initiate and/or terminate the supply of radiofrequency energy and fluid with one or more electrosurgical hand pieces that may be electrically coupled to the ESU 10. In an exemplary configuration, the ESU 10 includes a first receptacle 16, which may be a 3-pin connector configured to receive and electrically couple with a first electrosurgical hand piece 18 configured to deliver bipolar radiofrequency energy to tissue. The ESU 10 may further include a second receptacle 20, for example, a 7-pin receptacle, configured to receive and electrically couple with a second electrosurgical hand piece 22 configured to deliver at least one of monopolar radiofrequency energy or a combination of bipolar radiofrequency energy and monopolar radiofrequency energy. In an exemplary configuration, the second electrosurgical hand piece 22 is an electrosurgical hand piece constructed in accordance with the principles of the electrosurgical hand piece disclosed in pending U.S. application Ser. No. 14/688,723 entitled TELESCOPING DEVICE WITH SALINE IRRIGATION LINE, the entirety of which is expressly incorporated herein by reference.

The first receptacle 16 and the second receptacle 20 may be electrically coupled to switching circuit 24 of the generator 12 configured to allow simultaneous operation of the electrosurgical hand pieces 18 and 22 in the first receptacle 16 and the second receptacle 20. The switching circuit 24 may include an active bipolar radiofrequency output 26, a return bipolar radiofrequency output 28, and an active radiofrequency monopolar output 30 all electrically couplable together and to the first receptacle 16 and the second receptacle 20 through a plurality of relays 32. In particular, the first receptacle 16 may be in electrical communication with a first relay 32a and a second relay 32b disposed between the return bipolar radiofrequency output 28 and the first receptacle 16. The return bipolar radiofrequency output 28 is further disposed between the first relay 32a and the second relay 32b. A third relay 32c may also be electrically coupled to the first receptacle 16, the third relay 32c being disposed between the first receptacle 16 and the active bipolar radiofrequency output 26. Accordingly, the second relay 32b may be disposed between the first relay 32a and the third relay 32c.

When the generator 12 is operating in a mode to deliver electrical energy to both the first receptacle 16 and the second receptacle 20 for simultaneous operation of the electrosurgical hand pieces 18 and 22, the first relay 32a is set in an open position, the second relay 32b is set in a closed position, and the third relay 32c is set in a closed position. In such a configuration, current transmitted from the active bipolar radiofrequency output 26 is relayed toward the first receptacle 16 and current transmitted from the return bipolar radiofrequency output 28 is also transmitted to the first receptacle 16. Bipolar radiofrequency energy alternates from being transmitted from the return bipolar radiofrequency output 28 and the active bipolar radiofrequency output 28 to avoid a DC bias during bipolar radiofrequency treatment of tissue which may harm the patient. During simultaneous operation of the electro surgical hand pieces 18 and 20, the first relay 32a is open, which prevents bipolar radiofrequency current from being transmitted to the second receptacle 20.

The second receptacle 20 is configured to receive and electrically couple with the second electrosurgical hand piece 22. In one configuration, the second electrosurgical hand piece 22 is a combination electrosurgical hand piece configured to deliver both monopolar and bipolar radiofrequency energy and, in another configuration, the second electrosurgical hand piece 22 is an electrosurgical hand piece configured to deliver monopolar energy only. Accordingly, the second receptacle 20 is configured to receive multiple types of hand pieces. In an exemplary configuration, the second electrosurgical hand piece 22 includes an EEPROM 34 configured to communicate the type of hand piece is coupled to the generator 12. For example, the EEPROM 34 may determine that the second electrosurgical hand piece 22 is an electrosurgical hand piece configured to deliver both monopolar and bipolar radiofrequency energy. If bipolar energy is requested by the user, the relays 32 are set such that bipolar energy is delivered only to the second receptacle 20 and not to the first receptacle 16. If either a monopolar only electrosurgical hand piece 22 is electrically coupled to the second receptacle 20 or monopolar energy is selected from a combination second electrosurgical hand piece 22, a controller 36 in communication with the EEPROM 34 determines that monopolar energy is to be delivered to the second receptacle 20 and allows for simultaneous delivery of monopolar and bipolar energy.

Figure 2:
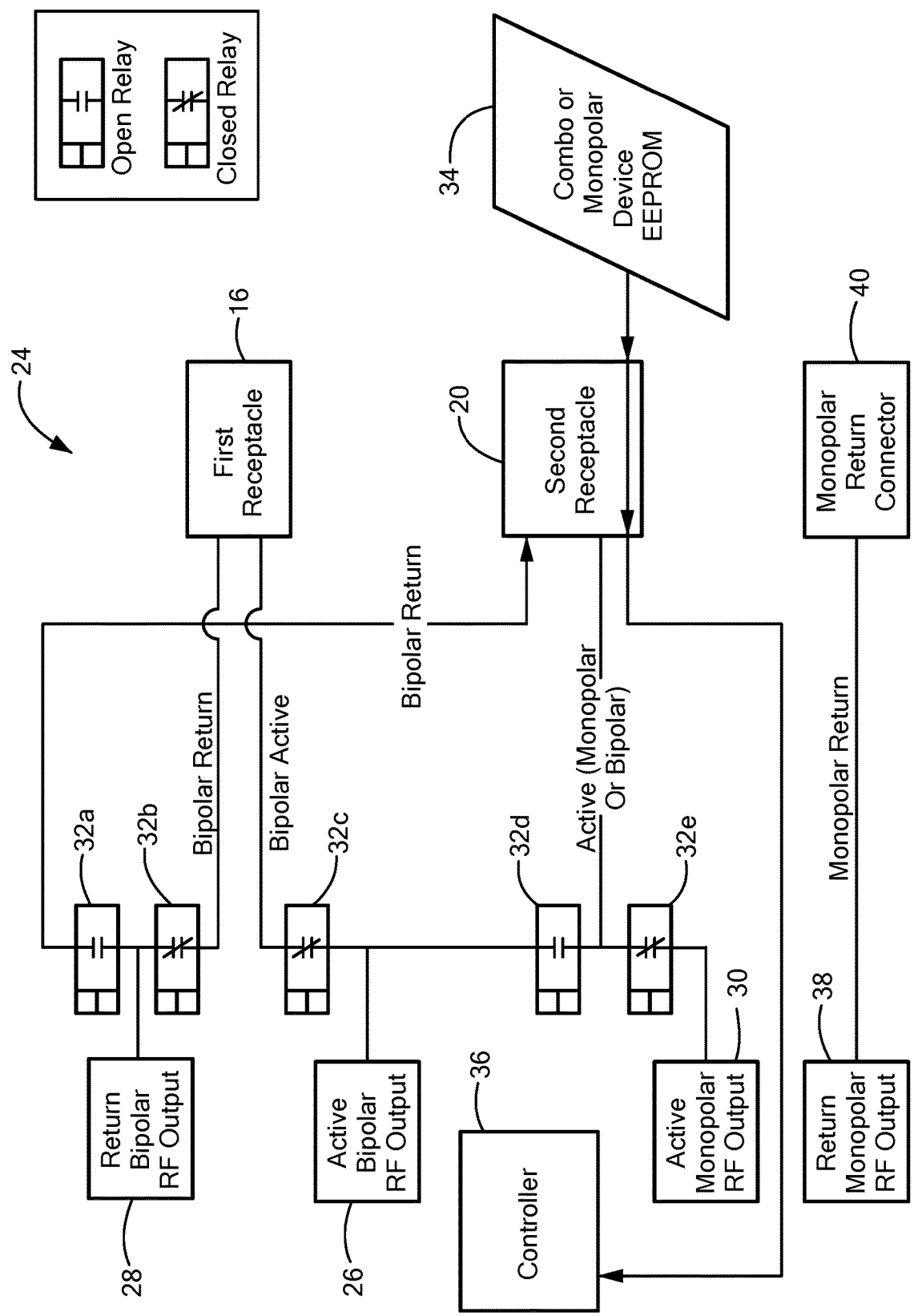
FIG. 2 is a circuit diagram of a switching circuit of a radiofrequency generator of the electrosurgical unit shown in FIG. 1.

Continuing to refer to FIG. 2, the second receptacle 20 is configured to be electrically couplable to the active bipolar radiofrequency output 26, the return bipolar radiofrequency output 28, and the active radiofrequency monopolar output 30. In particular, the active radiofrequency monopolar output 30 is configured to provide monopolar radiofrequency energy to the second receptacle 20 simultaneously with the active bipolar radiofrequency output 26 and/or the return bipolar radiofrequency output 28 providing bipolar energy to the first receptacle 16. To that end, a fourth relay 32d and a fifth relay 32e are electrically coupled to the second receptacle 20. In an exemplary configuration, the fourth relay 32d is disposed between the third relay 32c and the fifth relay 32e. Moreover, the fifth relay 32e is disposed between the active radiofrequency monopolar output 30 and the fourth relay 32d. In such a configuration, when the second receptacle 20 is configured to provide radiofrequency energy simultaneously with the first receptacle 16.

In an exemplary operation of the switching circuit 24 to provide for simultaneous radiofrequency energy delivery to the first electrosurgical hand piece 18 and the second electrosurgical hand piece 22, when the first electrosurgical hand piece 18 is electrically coupled to the first receptacle 16, the first relay 32a is set in an open configuration and the second relay 32b and the third relay 32c are set in a closed configuration. Such a configuration allows both the active bipolar radiofrequency output 26 and the return bipolar radiofrequency output 28 to transmit radiofrequency energy to the first receptacle 16 through the third relay 32c and the second relay 32b respectively, which transfer the bipolar radiofrequency to the first electrosurgical hand piece 18. When the second electrosurgical hand piece 22, whether a monopolar only hand piece or a combination of monopolar or bipolar hand piece is electrically coupled to the second receptacle 20, the EEPROM 34 determines which second electrosurgical hand piece 22 is coupled to the second receptacle 20, and determines if monopolar energy is selected to be delivered. If monopolar energy is selected by the user to be used in the second receptacle 20, the controller 36 sets the relays 32 for simultaneous radiofrequency energy delivery to the first electrosurgical hand piece 18 and the second electrosurgical hand piece 22. In particular, the fourth relay 32d is set to an open configuration and the first relay 32e is set to a closed position such that monopolar radiofrequency energy transmitted from the active monopolar radiofrequency output is relay to the second receptacle 20 through the fifth relay 32e. The monopolar radiofrequency energy may then be transmitted from the second electrosurgical hand piece 22 to the patient and returned to the generator from a return monopolar radiofrequency output 38, which may be a grounded back plate, and back into the generator 12 through a monopolar return connector 40.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An electrosurgical unit, comprising:
   a radiofrequency generator configured to generate electrosurgical energy the radiofrequency generator including:
      a first receptacle configured to electrically couple with a first electrosurgical hand piece configured to deliver bipolar radiofrequency energy, the first receptacle being electrically couplable to an active bipolar radiofrequency output, a return bipolar radiofrequency output, and an active monopolar radiofrequency output, a first relay and a second relay being disposed between the return bipolar radiofrequency output and the first receptacle, and a third relay disposed between the first receptacle and the active bipolar radiofrequency output;
      a second receptacle being electrically couplable to the active monopolar radiofrequency output, the active bipolar radiofrequency output, the active monopolar radiofrequency output, and a fourth relay and a fifth relay disposed between the second receptacle and the active monopolar radiofrequency output, the second receptacle being configured to electrically couple with:
         a second electrosurgical hand piece configured to deliver both monopolar radiofrequency energy and bipolar radiofrequency energy; and
         a third electrosurgical hand piece configured to deliver monopolar radiofrequency energy; and
   the radiofrequency generator including a relay circuit configured to allow simultaneous radiofrequency energy delivery to the electrosurgical hand pieces in the first receptacle and the second receptacle when the first electrosurgical hand piece is electrically coupled to the first receptacle when the first relay is open, the second relay is closed, the third relay is closed, the fourth relay is open, and the fifth relay is closed and at least one of:
      the second electrosurgical hand piece is electrically coupled to the second receptacle and the second hand piece is activated to deliver monopolar radiofrequency energy; and
      the third electrosurgical hand piece is electrically coupled to the second receptacle.

2. The electrosurgical unit of claim 1, wherein the fourth relay is disposed between the third relay and the fifth relay.

3. The electrosurgical unit of claim 2, wherein the fifth relay is disposed between the fourth relay and the active monopolar radiofrequency output.

4. The electrosurgical unit of claim 3, wherein the active bipolar radiofrequency output is disposed between the third relay and the fourth relay.

5. An electrosurgical unit, comprising:
   a radiofrequency generator configured to generate electrosurgical energy the radiofrequency generator including:
      a first receptacle configured to electrically couple with a first electrosurgical hand piece configured to deliver bipolar radiofrequency energy, the first receptacle being electrically coupled to an active bipolar radiofrequency output and a return bipolar radiofrequency output, a first relay and a second relay disposed between the return bipolar radiofrequency output and the first receptacle, and a third relay disposed between the first receptacle and the active bipolar radiofrequency output;
      a second receptacle being electrically couplable to the active bipolar radiofrequency output, the second receptacle being configured to electrically couple with at least one of:
         a second electrosurgical hand piece configured to deliver both monopolar radiofrequency energy and bipolar radiofrequency energy; and
         a third electrosurgical hand piece configured to deliver monopolar radiofrequency energy;
   the radiofrequency generator including a relay circuit configured to allow simultaneous radiofrequency energy delivery to the electrosurgical hand pieces in the first receptacle and the second receptacle when the first electrosurgical hand piece is electrically coupled to the first receptacle when the first relay is open, the second relay is closed, and the third relay is closed and at least one of:
      the second electrosurgical hand piece is electrically coupled to the second receptacle and the second hand piece is activated to deliver monopolar radiofrequency energy; and
      the third electrosurgical hand piece is electrically coupled to the second receptacle.

* * * * *